United States Patent [19]

Cross

[11] 4,324,242
[45] Apr. 13, 1982

[54] FEMININE SYRINGE

[75] Inventor: Marvin G. Cross, Vernon Hills, Ill.

[73] Assignee: Abbott Laboratories, North Chicago, Ill.

[21] Appl. No.: 193,785

[22] Filed: Oct. 3, 1980

[51] Int. Cl.³ .............................................. A61M 1/00
[52] U.S. Cl. ..................................... 128/232; 128/251
[58] Field of Search ............... 128/232, 231, 224, 251, 128/239

[56] References Cited

U.S. PATENT DOCUMENTS

| | | | |
|---|---|---|---|
| 2,297,994 | 10/1942 | Vellinga | 128/251 |
| 2,722,933 | 11/1955 | Allen | 128/231 |
| 3,693,783 | 9/1972 | Hart | 128/232 X |
| 4,225,062 | 9/1980 | Sneider | 128/251 |

*Primary Examiner*—John D. Yasko
*Attorney, Agent, or Firm*—Neil E. Hamilton; Robert L. Niblack

[57] ABSTRACT

A two-step release valve unit for a feminine syringe wherein a valve member and nozzle serve to open and close a dispensing port for an expandable syringe bag. The valve unit includes a slidable nozzle member which in one position will open a valve element. A two-step frictional engagement is provided between the nozzle member and the valve member housing so that the nozzle is retentively held out of contact with the valve element in a first position yet can be released therefrom to engage and open the valve element in the second position. When the nozzle member is removed, the bag is easily filled through a filling orifice in the valve member.

9 Claims, 5 Drawing Figures

FEMININE SYRINGE

BACKGROUND OF THE INVENTION

This invention relates to a syringe unit which utilizes an expandable bag and to a unique simplified filling and dispensing system which will permit filling of the bag as well as dispensing of its contents. More particularly, this invention is concerned with a dispensing means for an expandable syringe which employs few parts in its construction and affords a two-step valving action in delivering the bag contents through a pipe or nozzle member.

Syringe units of the type concerned with in this invention are described in U.S. Pat. Nos. 1,241,352; 2,297,944; 2,722,933; 3,110,311; 3,707,972 and 3,993,070. In U.S. Pat. Nos. 1,241,352 and 2,297,994 nozzle members are described for opening flap-type valves in fluid containers. Ribbed or flanged nozzles for use with syringe bags are disclosed in U.S. Pat. Nos. 2,722,933 and 3,933,070. A spring biased valve for a douche device is shown in U.S. Pat. No. 3,110,311 whereas U.S. Pat. No. 3,707,972 discloses a flanged connector for mating with a frusto-conical member.

The prior art does not disclose a valving arrangement for an expandable syringe wherein the nozzle can be temporarily but positively positioned out of contact with a valve member yet can subsequently activate the valve. Neither is the prior art concerned with an expandable syringe of the type previously described which employs a minimum number of parts and can be fabricated in an economical manner.

It is an advantage of the present invention to provide a simplified valve and dispensing pipe for an expandable syringe. Other advantages are a dispensing valve arrangement for an expandable syringe which is actuated by a nozzle member and the valve is held in a positive closed position prior to dispensing; an expandable syringe unit which can be disassembled to permit access for filling purposes; a combined valve and dispensing pipe for an expandable douche bag which will afford a two-step function between the valve and pipe for closure and activation; and an expandable syringe unit which is reusable and is easily operated.

SUMMARY OF THE INVENTION

The foregoing advantages are accomplished and the shortcomings of the prior art are overcome by the combined valve and dispensing pipe for an expandable syringe which includes a hollow nozzle having a head with a hollow spray stem and an inlet portion. An expandable bag has a neck portion to receive a valve member defined by a nozzle actuated portion, a nozzle receiving portion and a filling portion. Means are provided to secure the neck portion of the bag to the valve member. Frictional engagement means are defined by the inlet portion of the nozzle and the nozzle receiving portion of the valve member which will retentively position the inlet portion of the nozzle in a spaced relationship with respect to the nozzle actuated portion in a first position and to contact and open the nozzle actuated portion in a second position. The nozzle member can be detached from the valve member and a filling pipe or faucet heat can be inserted over the filling portion or orifice to fill the bag with a liquid. Subsequently, the inlet portion of the nozzle can be operatively positioned in the nozzle receiving portion. The frictional engagement means will position the inlet portion of the nozzle away from the nozzle actuated portion and upon movement of the nozzle inlet portion in the direction of the bag, it will open the nozzle actuated portion and provide fluid communication with the liquid in the bag.

In a preferred manner, the nozzle actuated portion of the valve member is a flap valve. The frictional engagement means is an annular flange extending inwardly from the nozzle receiving portion and an annular groove carried by the inlet portion of the nozzle. The frictional engagement means can further include shoulder portions positioned in both the valve nozzle receiving portion and the nozzle inlet portion. The shoulder portions are spaced from the flange and the groove but arranged for contact when the inlet portion of the nozzle opens the nozzle actuated portion of the valve member.

BRIEF DESCRIPTION OF THE DRAWINGS

A better understanding of the present combined filling and dispensing port for an expandable syringe will be accomplished by reference to the drawings wherein.

DESCRIPTION OF THE PREFERRED EMBODIMENT

Figure 1:
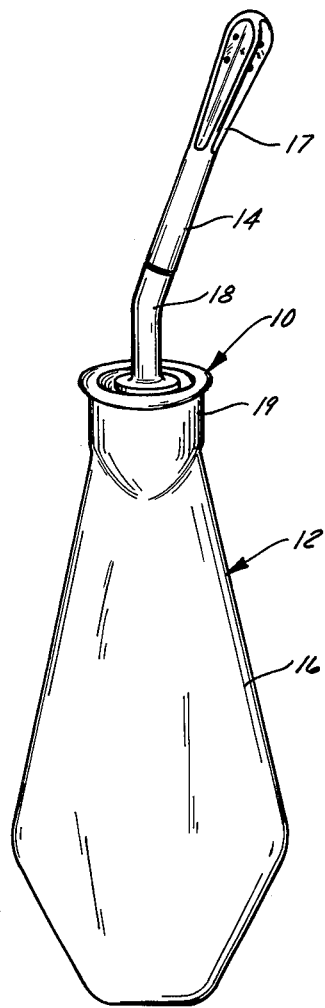
FIG. 1 is a side perspective view showing the assembled syringe unit prior to filling.

Proceeding to a detailed description of a preferred embodiment of the present invention, the combined valve and dispensing pipe 10 is shown as part of an expandable syringe unit 12 having the usual hollow nozzle or spray stem 14 of the feminine type and an expandable bag 16. The nozzle 14 is formed with a nozzle head 17 and a nozzle inlet 18.

Figure 2:
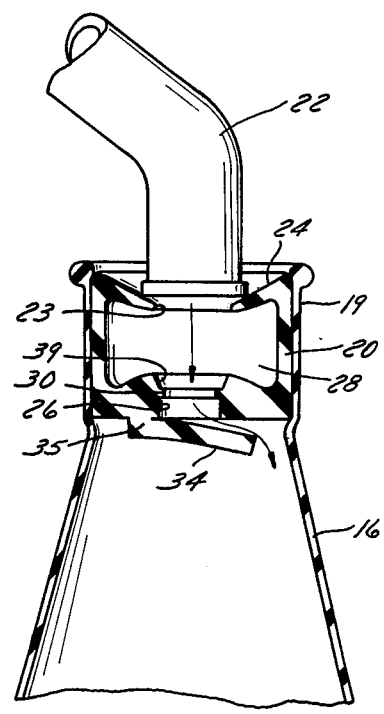
FIG. 2 is an enlarged partial view in vertical section showing the nozzle removed and the unit engaged by a faucet head for filling.

Referring specifically to FIG. 2, it will be seen that a valve member 20 is secured in neck 19 of bag 16 by means of an adhesive and the usual resiliency of the bag neck. Valve member 20 has an inwardly extending annular diaphragm 24 for sealable contact with faucet head 22. Annular diaphragm 24 provides an orifice 23 for filling bag 16 with water or a similar fluid. A second passageway 26 is disposed in valve element 20 and is normally closed by flap valve 34 hinged to valve member 20 by hinge section 35. The hinging will afford a biased closed positioned for flap valve 34. An inwardly extending flange 30 is located in passageway 26 and adjacent shoulder 39.

Figure 3:
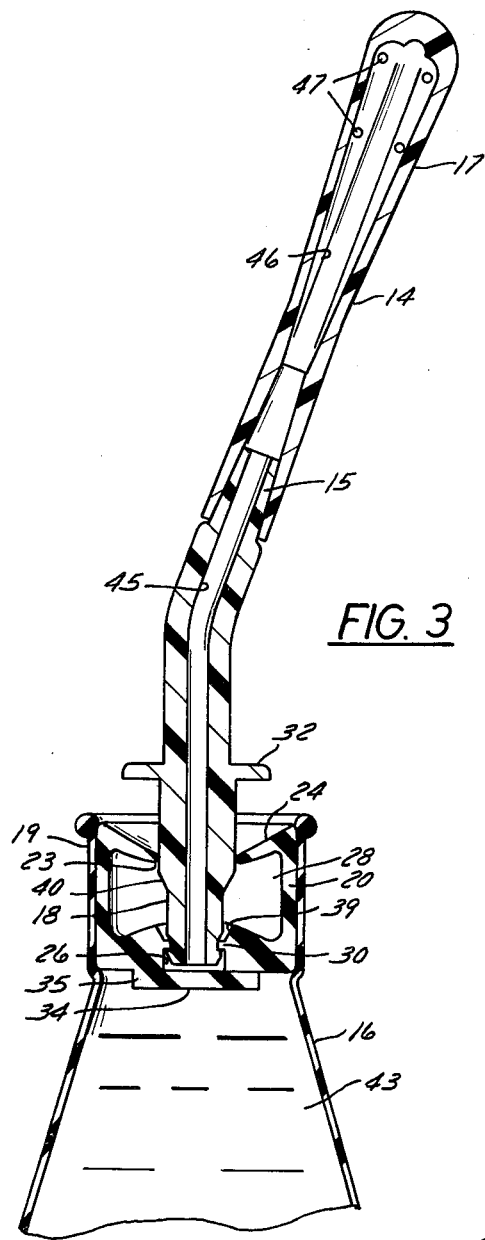
FIG. 3 is an enlarged view in vertical section illustrating the syringe unit after filling and prior to activation.
Figure 4:
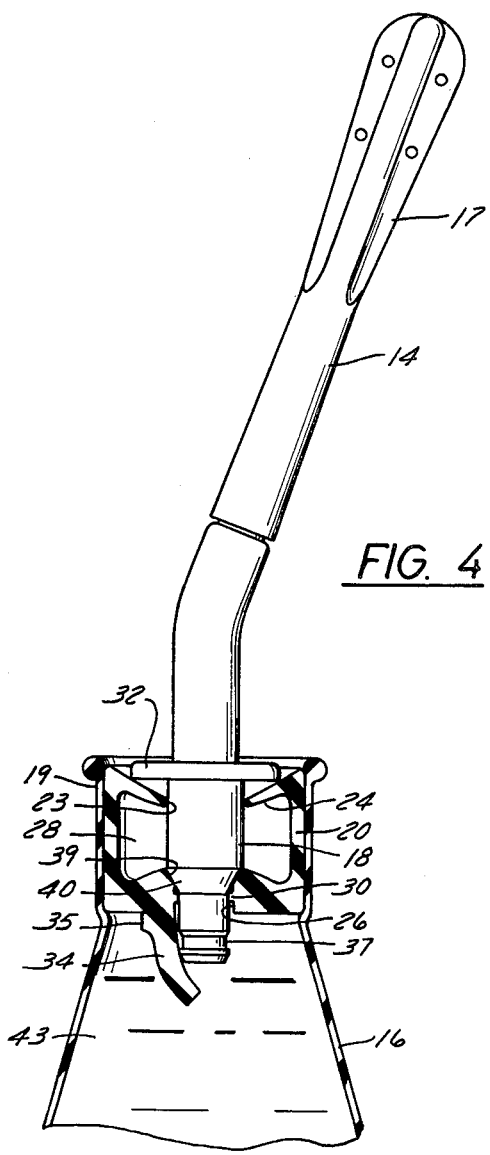
FIG. 4 is a view similar to FIG. 3 showing the syringe unit in the activated position.

As best seen in FIGS. 3 and 4, nozzle inlet portion 18 includes an annular groove 37 and a shoulder portion 40 spaced therefrom also extends from inlet portion 18 for contact with shoulder 39 of valve member 20. A flange 32 also extends from inlet portion 18 for contact with thin diaphragm 24. This is best seen in FIG. 4.

Figure 5:
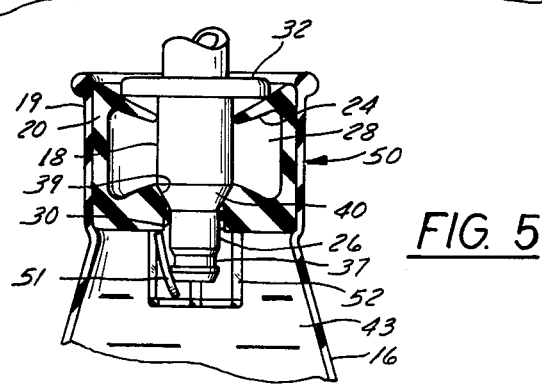
FIG. 5 is a view similar to FIG. 4 showing an alternative embodiment.

Referring to FIG. 5, an alternative embodiment is shown therein. This syringe unit 50 utilizes basically the same components as a syringe unit 10 except that the valve member 20 has a different valve element. In this instance, a freely movable valve element 51 is utilized and housed in cage member 52 which affords a restraining means. Valve element 51 will be floatable in liquid 43 so that when nozzle inlet portion 18 is positioned away from cage member 52, valve element 51 will close passageway 26 due to its buoyancy and the internal pressure in bag 16.

OPERATION

A better understanding of the advantages of the combined valve and dispensing pipe 10 and syringe unit 12 will be had by a description of their operation. The syringe unit 12 will preferably be packaged with the nozzle 14 removed from bag 16. When it is desired to fill bag 16 with liquid, preferably in the form of water, faucet head 22 will be placed over orifice 23 and in contact with diaphragm 24. Chamber 28 positioned in valve member 20 affords a filling portion. The force of the water entering the valve body will be sufficient to force flap valve 34 open permitting the water to flow into bag 16 through passageway 26. This is best seen in FIG. 2. As the liquid fills the bag 16 it will be appreciated that the construction of bag 16 is such that the walls will expand thus creating an expansive force on the contents of the bag. When the flow of liquid from the faucet ceases, the force of the liquid in the bag will cause flap valve 34 to close. Faucet heat 22 will then be removed from filling orifice 23. Nozzle 14 will have been supplied with bag 16 and will be in two pieces, namely 14 and 18. They will be interconnected through tapered fitment 15. (See FIG. 3) Nozzle inlet 18 will be placed in valve member 20 as shown in FIG. 3 so that flange 30 of valve member 20 will be received in groove 37 of nozzle inlet portion 18. This is best seen in FIG. 3 and shows the nozzle in the nozzle receiving portion of valve member 20 which is formed by chamber 28 and passageway 26. When it is desired to activate the syringe unit, a force will be exerted on nozzle 14 to move it in the direction of bag 16. This motion will cause the nozzle inlet portion 18 to contact flap valve 34 and at the same time projecting flange 30 to ride out of groove 37 in nozzle inlet 18. This movement will continue until shoulder 40 on nozzle inlet 18 will seat itself against shoulder 39 of valve member 20. At this point, the flap valve 34 will assume a position shown in FIG. 4. With flap valve 22 in the open position, liquid 43 under the pressure of bag 16 will automatically flow around the flap valve into the inlet portion 18 of nozzle 14 along channels 45, 46 and ultimately outwardly by means of ports 47 in head 17. It will be noted that when nozzle inlet portion 18 is in the second operating position shoulders 39 and 40 engage and flange 32 will also contact diaphragm 24. This is for the purpose of stability. When it is desired to deactivate the syringe all that is required is an outward pulling on nozzle 14 which will then cause flange 30 to reseat itself in groove 37 and flap valve 34 to assume a closed position as the nozzle inlet portion 18 moves to a position shown in FIG. 3.

During the previously described opening and closing of flap valve 34 it will be appreciated that nozzle 14, by means of the seating of flange 30 in groove 37, can be placed in a proper position before activation of the syringe. A positive holding of the nozzle and the valve in a closed position is afforded by this frictional engagement. It is only by an intentional subsequent force placed on nozzle 14 to move it in the direction of bag 16 that activation is effected. Accordingly, extensive manipulation of the nozzle 14 and bag 16 can be accomplished without fear of premature activation.

The syringe unit 50 shown in FIG. 5 will operate in the same manner as previously described for unit 12. The only difference will be in the manner in which the valve 51 is opened by nozzle inlet portion 18. This is effected merely by inlet portion 18 forcing valve 51 away from passageway 26. The syringe unit 50 will then operate as previously described for unit 12. Floatable valve 51 will be easily repositioned to close passageway 26 as its travel will be limited by cage member 52. Accordingly, when inlet portion 18 is moved to a position as indicated in FIG. 3, valve 51 by its buoyancy and the force of liquid 43 will cover passageway 26.

As previously described, nozzle 14 is formed from two components, head 17 and inlet portion 18. If desired, it could be formed as one, although it is preferable to have the head 17 formed from a rubber or Kraton material and inlet portion 18 formed from a rigid plastic material such as high density polyethylene. This is due to the face that nozzle 14 is preferably of the feminine type. However, other materials such as styrene could be employed. Valve member 20 and bag 16 are fabricated from rubber materials. If desired, flexible plastic could be substituted.

It will thus be seen that through the present invention there is now provided a combined valve and dispensing pipe for an expandable syringe which affords a two-step release feature between the valve and pipe. The syringe unit is actuated in a simple manner in that the contents of the bag are under pressure yet the valve mechanism is held in a positive closed position by means of a simple and unique interfitment between the nozzle member and the valve member. The syringe unit employs few parts, thus affording low cost fabrication.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A combined valve and dispensing pipe affording a two-step release actuation for an expandable syringe unit comprising:

a hollow nozzle defining a head with a hollow spray stem and an inlet portion;

an expandable bag having a neck portion;

a valve member defining a nozzle actuated portion, a nozzle receiving portion and a filling portion having an orifice carried in said valve member;

means to secure said neck portion of said bag to said valve member;

engagement means defined by said inlet portion of said nozzle and said nozzle receiving portion of said valve member, said engagement means includes a flange on said nozzle receiving portion of said valve and capture means for said flange on said inlet portion of said nozzle, said nozzle is retainable in a spaced relationship with respect to said nozzle actuated portion in a first position and to contact and open said nozzle actuated portion in a second position;

whereby said nozzle member can be detached from said valve member and a filling pipe or faucet head can be inserted over said filling orifice to fill said bag with a liquid and subsequently said inlet portion of said nozzle can be operatively positioned in said nozzle receiving portion and said engagement means will position said inlet portion of said nozzle away from said nozzle actuated portion, in a first position and upon movement of said nozzle inlet portion in the direction of said bag, said nozzle inlet portion will open said nozzle actuated portion and provide fluid communication with the liquid in said bag in a second position.

2. The combined valve and dispensing pipe as defined in claim 1 wherein said nozzle actuated portion of said valve member is defined by a flap valve.

3. The combined valve and dispensing pipe as defined in claim 1 wherein said filling portion of said valve member includes a thin diaphragm portion defining said orifice.

4. The combined valve and dispensing pipe as defined in claim 1 wherein said engagement means is defined in part by a flange extending inwardly from said nozzle receiving portion and said capture means is a groove carried by said inlet portion of said hollow nozzle.

5. The combined valve and dispensing pipe as defined in claim 4 wherein said flange and said groove are annular in configuration.

6. The combined valve and dispensing pipe as defined in claim 4 wherein said frictional engagement means further includes shoulder portions positioned on both said nozzle receiving portion and said nozzle inlet portion, said shoulder portions being spaced from said flange and said groove but arranged for contact when said inlet portion of said nozzle opens said nozzle actuated portion of said valve member.

7. The combined valve and dispensing pipe as defined in claim 3 further including a projecting flange extending from said nozzle inlet portion, said flange constructed and arranged to contact said thin diaphragm portion when said shoulder frictional engagement means is engaged and said nozzle inlet portion is in said second position.

8. The combined valve and dispensing pipe as defined in claim 1 wherein said head and said inlet portion of said hollow nozzle are formed in two separate parts.

9. The combined valve and dispensing pipe as defined in claim 8 wherein said nozzle is of the feminine type.

* * * * *